United States Patent
Cardosi et al.

(10) Patent No.: US 10,627,361 B2
(45) Date of Patent: Apr. 21, 2020

(54) ELECTROCHEMICAL TEST DEVICE

(71) Applicant: Inside Biometrics Limited, Dingwall (GB)

(72) Inventors: Marco Cardosi, Dingwall (GB); Stephanie Kirkwood, Dingwall (GB)

(73) Assignee: INSIDE BIOMETRICS INTERNATIONAL LIMITED, Dingwall (GB)

( * ) Notice: Subject to any disclaimer, the term of this patent is extended or adjusted under 35 U.S.C. 154(b) by 160 days.

(21) Appl. No.: 15/569,841

(22) PCT Filed: Apr. 28, 2016

(86) PCT No.: PCT/GB2016/051229
§ 371 (c)(1),
(2) Date: Oct. 27, 2017

(87) PCT Pub. No.: WO2016/174456
PCT Pub. Date: Nov. 3, 2016

(65) Prior Publication Data
US 2018/0128766 A1    May 10, 2018

(30) Foreign Application Priority Data

Apr. 30, 2015    (GB) .................................. 1507506.2

(51) Int. Cl.
*G01N 27/327* (2006.01)
*C12Q 1/00* (2006.01)
*C12Q 1/32* (2006.01)

(52) U.S. Cl.
CPC ......... *G01N 27/3272* (2013.01); *C12Q 1/004* (2013.01); *C12Q 1/32* (2013.01); *G01N 27/3273* (2013.01)

(58) Field of Classification Search
CPC .... C12Q 1/004; C12Q 1/005; G01N 27/3272; G01N 27/3271
See application file for complete search history.

(56) References Cited

U.S. PATENT DOCUMENTS 5,589,326 A * 12/1996 Deng .................. C07F 15/0026
435/14
6,736,957 B1 * 5/2004 Forrow .................. C12Q 1/004
204/403.04

(Continued)

FOREIGN PATENT DOCUMENTS

EP    0794429 A1    9/1997
EP    1398626 A1    3/2004

(Continued)

OTHER PUBLICATIONS

EPO computer-generated English language translation of the Detailed Description section of Murase et al. JP 2009-244014 A, downloaded Jul. 2, 2019. (Year: 2009).*
Sundberg et al., "Nitrogen-Bound and Carbon-Bound Imidazole Complexes of Ruthenium Ammines," Journal of the American Chemical Society/96:2/Jan. 23, 1974 (Year: 1974).*

(Continued)

*Primary Examiner* — Alexander S Noguerola
(74) *Attorney, Agent, or Firm* — Tarolli, Sundheim, Covell & Tummino LLP (57) ABSTRACT

An electrochemical test device for determining a concentration of an analyte in a fluid sample is provided. The electrochemical test device comprises a set of electrodes including a working electrode for the analyte and sensing chemistry for the working electrode, wherein the sensing chemistry comprises a diaphorase, an electron transfer agent having a standard redox potential in the range of −0.52 to 0.18 V, an $NAD(P)^+$-dependent dehydrogenase and a cofactor for the $NAD(P)^+$-dependent dehydrogenase.

19 Claims, 7 Drawing Sheets

(56) References Cited

U.S. PATENT DOCUMENTS

| | | | |
|---|---|---|---|
| 6,821,410 B2 * | 11/2004 | Watanabe | C12Q 1/005 204/403.1 |
| 7,943,022 B2 * | 5/2011 | Teodorczyk | C12Q 1/001 204/403.01 |
| 8,303,801 B2 * | 11/2012 | Wilsey | C12Q 1/001 205/792 |
| 10,000,785 B2 * | 6/2018 | Jung | C12Q 1/004 |
| 2007/0131547 A1 | 6/2007 | Asahi | |

FOREIGN PATENT DOCUMENTS

| | | | | |
|---|---|---|---|---|
| JP | 2007225305 A | | 9/2007 | |
| JP | 2009-244014 A | * | 10/2009 | G01N 27/416 |
| JP | 2014160024 A | | 9/2014 | |
| WO | 9835232 A2 | | 8/1998 | |
| WO | 03097860 A1 | | 11/2003 | |
| WO | 2006067424 A1 | | 6/2006 | |
| WO | WO 2006/067424 A1 | * | 6/2006 | C12Q 1/32 |
| WO | 2007000596 A1 | | 1/2007 | |
| WO | WO 2007/072018 A2 | * | 6/2007 | C07F 15/00 |
| WO | 2010035048 A1 | | 4/2010 | |

OTHER PUBLICATIONS

Huynh et al., "Quinone 1 e– and 2 e– / 2 H+ Reduction Potentials: Identification and Analysis of Deviations from Systematic Scaling Relationships," Journal of the American Chemical Society, 2016, 138, 15903-15910, Nov. 10, 2016 (Year: 2016).*

Page 331 of "Dehydrogenases", editor: Rosa Angela Canuto, publisher: BoD Books on Demand, 2012 (Year: 2012).*

EPO computer-generated English language translation of the Description section of Komatsu et al. JP 2007-225305 A (Year: 2007).*

EPO computer-generated English language translation of the Description section of Kashiwagi et al. JP 2014-160024 A (Year: 2014).*

International Search Report and Written Opinion dated Jul. 21, 2016 for corresponding International Patent Application No. PCT/GB2016/051229.

GB Search Report dated Jan. 27, 2016 for corresponding GB Patent Application No. 1507506.2.

Sato F. et al., "Enzyme-based glucose fuel cell using Vitamin K3-immobilized polymer as as electron mediator", Electrochemistry Communications 7 (2005), pp. 643-647.

Fultz M L et al, "Mediator compounds for the electrochemical study of biological redox systems: a compilation", Analytica Chimica Acta, Elsevier, Amsterdam NL, vol. 140, No. 1, pp. 1-18, Aug. 1, 1982.

* cited by examiner

| 420 |
|---|
| 410 |
| 214 |

| 820 |
|---|
| 610 |
| 510 |

Fig. 8

| 620 |
|---|
| 910 |
| 510 |

Fig. 9

ELECTROCHEMICAL TEST DEVICE

RELATED APPLICATIONS

The present application is a U.S. National Stage application under 35 USC 371 of PCT Application Serial No. PCT/GB2016/051229, filed on 28 Apr. 2016; which claims priority from GB Patent Application No. 1507506.2, filed 30 Apr. 2015, the entirety of both of which are incorporated herein by reference.

TECHNICAL FIELD

The present invention relates to electrochemical test devices such as test strips for determining the concentration of an analyte in a fluid sample. In particular, the present invention relates to sensing chemistry for such electrochemical test devices.

BACKGROUND

The detection and measurement of substances, chemicals, or analytes in a bodily fluid sample is useful in a variety of applications, such as in fitness monitors or in the medical device industry. For example, an individual may choose to monitor a concentration of an analyte such as glycerol in his or her bloodstream in order to determine whether or not a chosen fitness regime is effective. Glycerol is a fitness related analyte associated with lipolysis and fat breakdown from stored body fat.

As another example, people with diabetes need to regularly monitor the concentration of glucose in their bloodstream in order to determine if they are in need of glucose or insulin or other diabetes medication. Diagnostic devices and kits have been developed over the years to allow a diabetic individual to autonomously determine the concentration of glucose in their bloodstream, in order to better anticipate the onset of hyperglycaemia or hypoglycaemia and take any necessary action.

When trying to ascertain a level of an analyte in, for example, a blood sample, an individual will typically perform a finger stick using a lancing device to extract a small drop of blood from a finger or alternative site. An electrochemical test device, which is often a test strip, is then inserted into a diagnostic meter, and the sample is applied to the test strip. Through capillary action, the sample flows through a capillary channel across a measurement chamber of the device and into contact with one or more electrodes or conductive elements coated with sensing chemistry for interacting with a particular analyte or other specific chemical (for example glucose) in the blood sample. The magnitude of the reaction is dependent on the concentration of the analyte in the blood sample. The diagnostic meter may detect the current generated by the reaction of the sensing chemistry with the analyte, and the result can be displayed to the individual.

Typically, such electrochemical test devices have a set of electrodes such as a counter/reference electrode and one or more working electrodes. Sensing chemistry is used which is typically tailored to the particular analyte or biometric of interest. An enzymatic electrode is a combination of an enzyme and an electrochemical transducer. The direct transfer of electrons between the enzyme and the electrode is generally not easy to achieve and so an electron transfer agent (or mediator) is sometimes used to carry electrons between the enzyme and the electrode to facilitate the electrocatalysis. For example, when measuring the concentration of glucose in a sample, a glucose oxidase or a glucose dehydrogenase enzyme can be used in conjunction with a mediator such as potassium ferricyanide. When detecting other analytes, different enzymes may be used, such as β-hydroxybutyrate dehydrogenase for measuring the ketone body β-hydroxybutyrate.

The NAD(P)$^+$-dependent dehydrogenases, such as glycerol dehydrogenase, require nicotinamide adenine dinucleotide (either in its oxidized form, NAD(P)$^+$ or reduced form, NAD(P)H) as a cofactor for the dehydrogenase. Since the dehydrogenases release NAD(P)$^+$/NAD(P)H from active sites reversibly, NAD(P)$^+$/NAD(P)H may function as the electron transfer agent in the dehydrogenase-modified electrodes. The direct oxidation of NAD(P)H at a carbon working electrode requires a large positive overpotential (for example 0.55 V) and so electrochemically active interferents may transfer electrons to the electrode, thereby interfering with the measurement of an analyte.

In a healthy individual, for some analytes such as glycerol or fP-hydroxybutyrate the concentrations of the analytes may be very low. Insensitive or inaccurate electrochemical test devices may take unreliable measurements of the concentration of such analytes. For measurements of some analytes, such as glycerol or fP-hydroxybutyrate, sensitive electrochemical test devices are desired.

The present invention seeks to provide an improved electrochemical test device for determining a concentration of an analyte in a fluid sample.

SUMMARY

An electrochemical test device is provided for determining a concentration of an analyte in a fluid sample. The electrochemical test device may comprise a set of electrodes including a working electrode for the analyte and sensing chemistry for the working electrode. The sensing chemistry may comprise a diaphorase. The sensing chemistry may comprise an electron transfer agent. The electron transfer agent may have a standard redox potential in the range of −0.52 to 0.18 V. The sensing chemistry may comprise an NAD(P)$^+$-dependent dehydrogenase. The sensing chemistry may comprise a cofactor for the NAD(P)$^+$-dependent dehydrogenase (either nicotinamide adenine dinucleotide (NAD$^+$) or nicotinamide adenine dinucleotide phosphate (NADP$^+$)).

Further optional features will be appreciated from the following description.

BRIEF DESCRIPTION OF THE DRAWINGS

Illustrative embodiments of the present disclosure will now be described, by way of example only, with reference to the drawings. In the drawings.

Throughout the description and the drawings, like reference numerals refer to like parts.

DESCRIPTION

The present invention seeks to provide an improved electrochemical test device for determining a concentration of an analyte in a fluid sample. Whilst various embodiments of the invention are described below, the invention is not limited to these embodiments, and variations of these embodiments may be made without departing from the scope of the invention.

Throughout this specification, reference is made to directional terms such as "above" and "below", or "upper" and "lower". References made to such terms are purely indicative of relative positions of the features of embodiments disclosed herein. For example, wherever there is mention of a cover above a spacer layer and an insulator layer below the spacer layer, it should be understood that the cover and the insulator layer are formed on opposite sides of the spacer layer. That is, directional terms such as those described herein do not refer to a direction relative to a viewpoint of an observer, but instead should be considered in all aspects as relative terms.

Various additional details of aspects of electrochemical test devices are described in the following commonly assigned patent applications (denoted collectively herein as the "related applications"). These related applications include the International patent application having attorney reference number P62546WO, entitled "Electrochemical test device" filed on 28 Apr. 2016; the International patent application, entitled "Electrochemical test device" filed on 28 Apr. 2016; the International patent application, entitled "Electrochemical test device" filed on 28 Apr. 2016; the International patent application, entitled "Electron Transfer Agent" filed on 28 Apr. 2016; the International patent application, entitled "System and method for measuring fitness-related parameters" filed on 28 Apr. 2016; and the International patent application, entitled "Electrochemical test device" filed on 28 Apr. 2016. The content of each of these related applications is hereby incorporated by reference herein in its entirety for all purposes.

The term "alkyl", used alone or as part of a larger moiety, refers to a straight or branched chain aliphatic group having from 1 to 12 carbon atoms. The alkyl group therefore has 1, 2, 3, 4, 5, 6, 7, 8, 9, 10, 11 or 12 carbon atoms. For purposes of the present disclosure, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

The term "amine" may refer to a primary, secondary or tertiary amine. The amine will generally be NRR'R", where R, R' and R" are each selected from hydrogen or alkyl. Any suitable alkyl group may be used. Preferred alkyl group will be $C_1$, $C_2$, $C_3$, $C_4$, $C_5$, $C_6$-Preferably, an amine is $NH_3$.

The term "heteroaryl" means a monocyclic or bicyclic radical of 5 to 12 ring atoms having at least one aromatic ring containing one, two, or three ring heteroatoms selected from N, O or S, the remaining ring atoms being C. The attachment point of the heteroaryl radical may be via the heteroatom. The heteroaryl rings may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The term "halide" refers to a substituent which is fluoro, chloro, bromo or iodo.

The term "substituted", as used herein, means that a hydrogen radical of the designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

An electron transfer agent (or redox mediator) is an agent for transferring electrons between an analyte or an analyte-reduced or analyte-oxidized enzyme and an electrode, either directly, or via one or more additional electron transfer agents.

An electrochemical test device is disclosed for determining a concentration of an analyte in a fluid sample. The electrochemical test device comprises a set of electrodes including a working electrode and sensing chemistry for the working electrode. The sensing chemistry comprises a diaphorase. The sensing chemistry further comprises an electron transfer agent having a standard redox potential in the range of −0.52 to 0.18 V. The electron transfer agent is for facilitating the transfer of electrons from the analyte to the working electrode. The electrochemical test device further comprises an $NAD(P)^+$-dependent dehydrogenase and a cofactor for the $NAD(P)^+$-dependent dehydrogenase.

Sensing chemistry typically comprises at least one reagent which interacts with an analyte in the fluid sample to produce, directly or indirectly, a detectable signal at the working electrode for the analyte. When producing the signal indirectly more than one reagent is usually involved.

By providing an electrochemical test device having sensing chemistry on a working electrode, the sensing chemistry including an electron transfer agent having a standard redox potential in the range of −0.52 to 0.18 V, a low overpotential is required for the oxidation of NAD(P)H and so, in use, there is little interference from other electrochemically active components of the fluid sample, for example uric acid. Accordingly, the presently disclosed electrochemical test device can perform a measurement of the analyte with little interference from other electroactive components of the fluid sample. The disclosed electrochemical test device is therefore more sensitive and provides a better analytical performance than other electrochemical test devices, and enables lower concentrations of an analyte in a fluid sample to be measured. The diaphorase catalyses the oxidation of NAD(P)H by an electron transfer agent and, accordingly, by utilising the diaphorase the oxidation of the NAD(P)H can occur at an appreciable rate. This allows the electrochemical test device to measure the analyte in a short window of time.

The diaphorase may be any suitable diaphorase. For example, the diaphorase may be an NADPH:acceptor oxidoreductase (NADPH dehydrogenase of the class EC 1.6.99.1). The diaphorase may be an NADH:acceptor oxidoreductase (NADH dehydrogenase of the class EC 1.6.99.3). The diaphorase may be an NADH:(quinone acceptor) oxidoreductase (NADH dehydrogenase (quinone) of the class EC 1.6.99.5).

The cofactor may be nicotinamide adenine dinucleotide ($NAD^+$). The cofactor may be nicotinamide adenine dinucleotide phosphate ($NADP^+$).

The electrochemical test device may be for determining a concentration of glycerol. The $NAD(P)^+$-dependent dehydrogenase may be glycerol dehydrogenase.

The electrochemical test device may be for determining a concentration of β-hydroxybutyrate. The $NAD(P)^+$-dependent dehydrogenase may be β-hydroxybutyrate dehydrogenase.

The electrochemical test device may be for determining a concentration of glucose. The $NAD(P)^+$-dependent dehydrogenase may be $NAD^+$-glucose dehydrogenase.

The sensing chemistry may be disposed on the working electrode in layers including a layer adjacent the working electrode. There may be two layers. The layer adjacent the working electrode may comprise the diaphorase. The layer adjacent the electrode may also comprise the electron transfer agent.

By disposing sensing chemistry in layers upon the working electrode, particular requirements of the $NAD(P)^+$-dependent dehydrogenase and the diaphorase can be addressed more efficiently for optimal performance by altering the makeup of individual layers. For example, the pH level of a particular layer may be altered using suitable buffer components or otherwise in order to optimize the performance of the $NAD(P)^+$-dependent dehydrogenase and the diaphorase.

The layers may include a layer which is not adjacent the working electrode. The layer which is not adjacent the working electrode may comprise the $NAD(P)^+$-dependent dehydrogenase.

The layer not adjacent the electrode may also comprise the cofactor. By providing the cofactor only in the layer not adjacent the electrode, the background noise of the analyte measurement is reduced, further improving the sensitivity of the electrochemical test device. Furthermore, by providing the cofactor only in the layer not adjacent the electrode, the production process of the electrochemical test devices is greatly simplified and the reagents are used efficiently. Furthermore, by providing the cofactor in the same layer as the $NAD(P)^+$-dependent dehydrogenase, the diffusion distances between the cofactor and the dehydrogenase are reduced. Accordingly, there is an improvement to the electrode response and performance when measuring an analyte in a fluid sample.

The electron transfer agent may be ruthenium hexaammine trichloride. The electron transfer agent may be a ruthenium- or osmium-based electron transfer agent.

The ruthenium- or osmium-based electron transfer agent may be a complex of formula (1), $$[M(A)_x(B)_y](X)_n \quad (1)$$

wherein M is ruthenium or osmium, A is an amine ligand, each B is a ligand different to A, x is an integer selected from 1 to 5, y is an integer selected from 1 to 5, x+y is 6 or 8, n is an integer selected from 1 to 6, and X is any suitable counterion.

M may be ruthenium. For example, M may be Ru(II) or Ru(III). The oxidation state of the metal M in the complex may be selected to be 2+, 3+ or 4+.

A may be NRR'R", wherein R, R' and R" are independently selected from hydrogen or alkyl. A may be $NH_3$. It will be appreciated that when x is two or more, all "A" may be the same.

Each B is a ligand different to A. It will be appreciated that when y is 2 or more, B may be the same or different. B may be independently selected from a halide or optionally substituted heteroaryl. When B is an optionally substituted heteroaryl, the heteroaryl may be optionally substituted with an optionally substituted $C_{1-6}$ alkyl. B may be a halide, and the halide may be selected from the group consisting of $F^-$, $Cl^-$, $Br^-$, $I^-$. B may be chloride. B may be pyridyl, or 4-methyl pyridyl.

It will be appreciated that A and B may be selected such that the overall charge on the complex of formula (1) is selected from the group +2, +1, 0, −1, −2 and −3.

The counterion X may be a counterion selected to lead to the charge neutrality of $[M(A)_x(B)_y]$. The counterion X may be selected from $F^-$, $Cl^-$, $Br^-$, $I^-$, $PF_6^-$.

The ruthenium complex may be [Ruthenium$^{III}$(NH$_3$)$_5$Cl]X (ruthenium pentaammine chloride). The ruthenium complex may be [Ruthenium$^{III}$(NH$_3$)$_5$Cl].2Cl.

The ruthenium- or osmium-based electron agent may be a ruthenium-based electron transfer agent. The concentration of the ruthenium-based electron transfer agent in the sensing chemistry may be from 8% to 15% by weight before drying of the sensing chemistry.

Transition metal complexes of the present disclosure can be soluble in water or other aqueous solutions. In general, the transition metal complexes can be made soluble in aqueous solvents by having an appropriate counterion or ions, X. The solubility of the transition metal complex may be greater than about 0.025M at 25° C. in water.

The sensing chemistry may comprise between about 0.3%-2% (w/w) diaphorase. The sensing chemistry may comprise about 1% (w/w) diaphorase.

The diaphorase may be dissolved in a buffer such as, for example, phosphate or citrate. The buffer may be Tris buffer. The pH of the buffer may be about 7.

The sensing chemistry may comprise a phosphate or Tris buffer. The pH of the buffer may be in the range of about 6.5-7.5. For example, the pH of the buffer may be about 7. The pH of the buffer may be in the range of about 9.5-11. For example, the pH of the buffer may be about 10.5. The buffer may be of any suitable pH.

The diaphorase may have an enzyme activity range of from about 75 kU to 200 kU per 100 grams composition. The enzyme activity range is selected so that the analyte current does not depend on the level of enzyme activity in the composition and to avoid solubility issues for too high levels of diaphorase.

The sensing chemistry may comprise between about 0.07%-0.13% (w/w) flavin mononucleotide (FMN). The sensing chemistry may comprise 0.1% (w/w) FMN.

The sensing chemistry may comprise about 0.5%-3.5% (w/w), or 2.5%-3.5% (w/w), hydroxyethyl cellulose (HEC). The sensing chemistry may comprise 3% HEC.

In the context used herein, "about" may refer to a variation of ±10% of the numerical value.

An apparatus is provided, the apparatus configured to determine the concentration of an analyte in a fluid sample applied to an electrochemical test device as described herein. The apparatus may comprise circuitry for receiving a signal from the electrochemical test device such as an output signal generated from a fluid sample applied to the electrochemical test device. The apparatus may further comprise a memory storing instructions to determine the concentration of the analyte with reference to the received signal. The memory may also store data for the instructions to refer to, for example data mapping the output signal to analyte concentration, or a function of the output signal to be calculated. The apparatus may further comprise a processor configured to perform the instructions stored in the memory.

Figure 1:
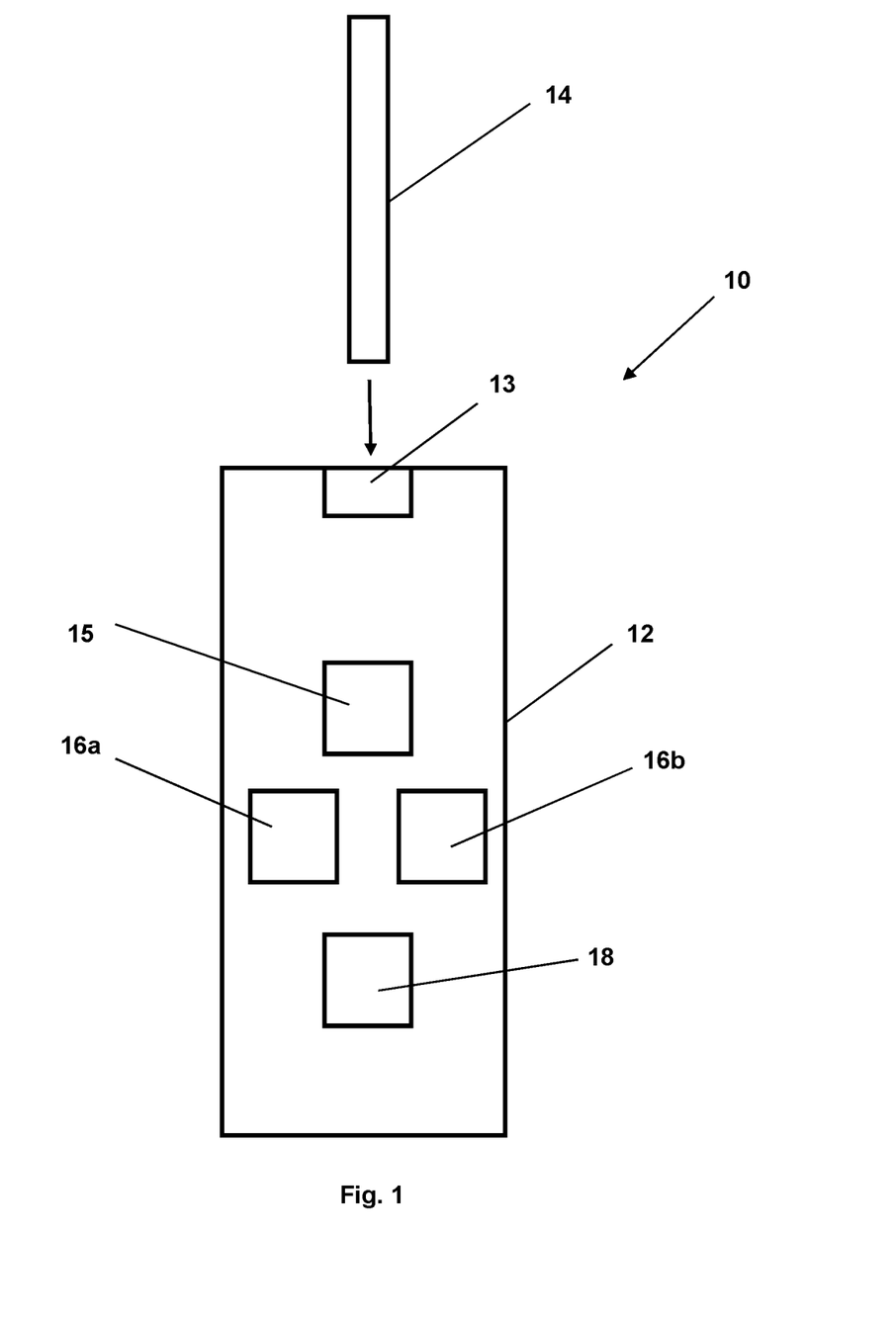
FIG. 1 shows a strip-meter system.

FIG. 1 shows an apparatus in the form of a strip meter system 10. System 10 comprises a meter 12 for receiving an output signal from an electrochemical test device such as electrochemical test strip 14. Electrochemical test strip 14 comprises a set of electrodes which typically comprises one or more working electrodes (not shown in FIG. 1) and a counter/reference electrode, each of the working electrodes provided with sensing chemistry for reacting with at least one analyte of a fluid sample to be applied to electrochemical test strip 14. In this example, each of the one or more working electrodes has reagents coated thereon. The counter/reference electrode may also have reagents coated thereon. Meter 12 comprises receiving means 13 for receiving electrochemical test strip 14 and applying a potential difference to the working electrode(s) and the counter/reference electrode.

Meter 12 further comprises processing circuitry 15 for carrying various functions relating to the operation of meter 12. For example, processing circuitry 15 is configured to control operation of receiving means 13 so as to control application of a potential difference between the working electrode(s) and the counter/reference electrode. Processing circuitry 15 is further configured to process one or more output signals generated at test strip 14 and to control a display of messages on display 18. The processing circuitry may perform other functions. Meter 12 further comprises first and second memory storages 16a and 16b. Although two memory storages are shown, in other embodiments the memory storages may be combined to form a single memory storage, or meter 12 may comprise more than two memory storages. Meter 12 also comprises a display 18 for displaying readouts of measurements taken by meter 12.

When manufacturing an electrochemical test device such as electrochemical test strip 14 the device can be constructed in layers with different layers providing different features such as conductive tracks, electrode area definition and positioning of chemistry. Suitable manufacturing techniques may be used such as deposition techniques (e.g. printing such as thick-film printing methods including screen printing, rotary printing, serigraph printing, gravure printing and sub-microlitre controlled volume drop on demand printing technologies) and adherence of layers, as will be apparent from the following.

Figure 2:
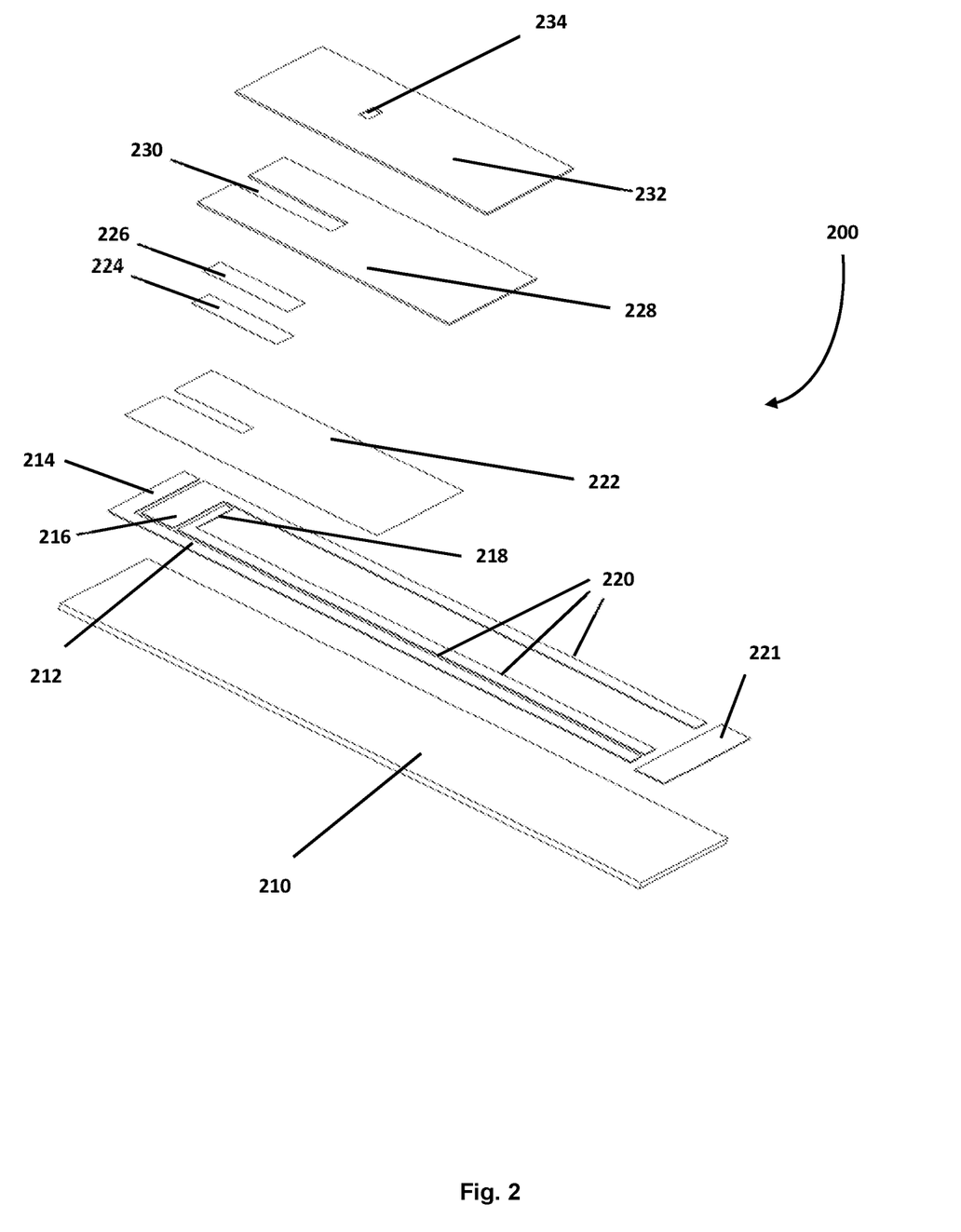
FIG. 2 shows an exploded view of an electrochemical test device.

FIG. 2 shows a perspective, exploded view of an electrochemical test device in the form of electrochemical test strip 200 according to a first example. This example will be described in relation to a received blood sample of around 0.5 µl in volume, although the electrochemical test strip could be used with any suitable fluid sample. The electrochemical test strip shown in FIG. 2 has an end-fill configuration i.e. the blood sample can be received at one end of the electrochemical test device 200.

The electrochemical test strip 200 comprises a support layer or substrate 210. Substrate 210 has a thickness of around 0.35 mm. The substrate 210, in this example, is made from polyester, although any suitable substrate may be used.

The substrate 210 is thermally and dimensionally stable, with consistent properties such as thickness, surface roughness and surface energy.

Above the substrate 210 is the conductor layer 212. In this example, the conductor layer 212 is directly disposed upon the substrate 210 using carbon-based ink. In this example, the conductor layer 212 is printed directly onto the upper surface of the substrate 210. The conductor layer 212 may be printed onto the substrate 210 using screen printing, lithographic printing, tomographic printing, sub-microlitre controlled volume drop on demand printing technologies, or any other suitable method of printing. The conductor layer comprises a set of electrodes including working electrode 214, counter/reference electrode 216 and fill-sufficiency detect electrode 218. The conductor layer 212 further comprises a set of conductive tracks 220. In this example, the conductive tracks 220 extend along the longitudinal axis of the electrochemical test strip 200. The conductive tracks are suitable for electrically coupling the electrodes to a meter 12. The conductor layer 212 further comprises a switch-on bar 221 for activating a meter 12.

Above the conductor layer 212 is an insulating layer 222. The insulator layer 222 is made of an electrically insulating material, and is directly disposed upon the upper surface of the conductor layer 212. The insulator layer 222 is, in this example, made of a dielectric material and defines an interaction area. That is, the insulation layer 222 electrically insulates some portions of the conductor layer 212 from the layers situated above in the electrochemical test strip 200. Specially designed gaps in the insulator layer 222 expose some portions of the conductor layer 212 to the layers situated above in the electrochemical test strip 200.

Sensing chemistry is applied to the electrodes of the conductor layer 212. In this example, the sensing chemistry comprises two reagent layers 224 and 226 which are applied to exposed electrode interaction areas after the insulator layer 222 is formed. The reagent layers 224 and 226 coat the exposed electrode interaction areas. In this way, the insulator layer 222 defines which part or parts of the electrodes of the conductor layer 212 are able to come into contact with an applied blood sample for the measurement of the analyte. The sensing chemistry of the reagent layers will be discussed in further detail below.

Above the insulator layer 222 is a spacer layer 228 formed of a polyester core. The spacer layer 228 defines a sample introduction channel 230, or measurement chamber, for introducing a blood sample to the conductor layer 212. The height of the sample introduction channel 230 is defined by the thickness of the spacer layer 228. The spacer layer 228 is formed of double sided adhesive tape which, in this example, is applied directly to the upper surface of the insulator layer 222. The sample introduction channel 230 is formed by providing a gap into the double sided adhesive tape of the spacer layer 228. The thickness of the spacer layer 228 is approximately 0.1 mm, which provides a good balance between the volume of the sample introduction channel and the performance of the electrochemical test strip 200.

Above the spacer layer 228 is a cover layer 232. During manufacture, the spacer layer 228 and the cover layer 232 may be applied to the test strip 200 separately or as a single prelaminated layer, although in this example the cover layer 232 is a separate layer to the spacer layer 228. The cover layer 232 acts as a ceiling to the sample introduction channel 230, thereby substantially closing the sample introduction channel 230 from above. The cover layer 232 is formed of single sided tape and, in this example, is adhered directly to the upper surface of the spacer layer 228. The lower surface of the cover layer 232 has hydrophilic properties, which assist in drawing a blood sample into the sample introduction channel 230. The cover layer 232 further has a vent 234 suitable for venting air out of the sample introduction channel 230 to allow a blood sample to enter the sample introduction channel 230 via capillary action. The vent 234 is narrower than the sample introduction channel 230 so that air may easily vent from the sample introduction channel 230 but blood or any other fluid will not easily be able to pass through the vent 234.

In use, a fluid sample is provided to the electrochemical test device and a potential difference is applied across the fluid sample to generate a detectable output signal indicative of an analyte concentration in the fluid sample. In this example, in use a blood sample is applied to the sample introduction channel 230 of the electrochemical test strip 200. Through capillary action, the blood is drawn into the sample introduction channel 230 to the electrodes 214, 216 and 218 of the conductor layer 212. That is, the sample introduction channel 230 acts as a capillary channel. A potential difference is applied across the electrodes 214 and 216 and the blood sample, and an output signal such as a transient current is generated from the blood sample. The characteristics of the output signal can be used to determine the concentration of an analyte, such as glucose, glycerol or β-hydroxybutyrate, in the blood sample.

Figure 3:
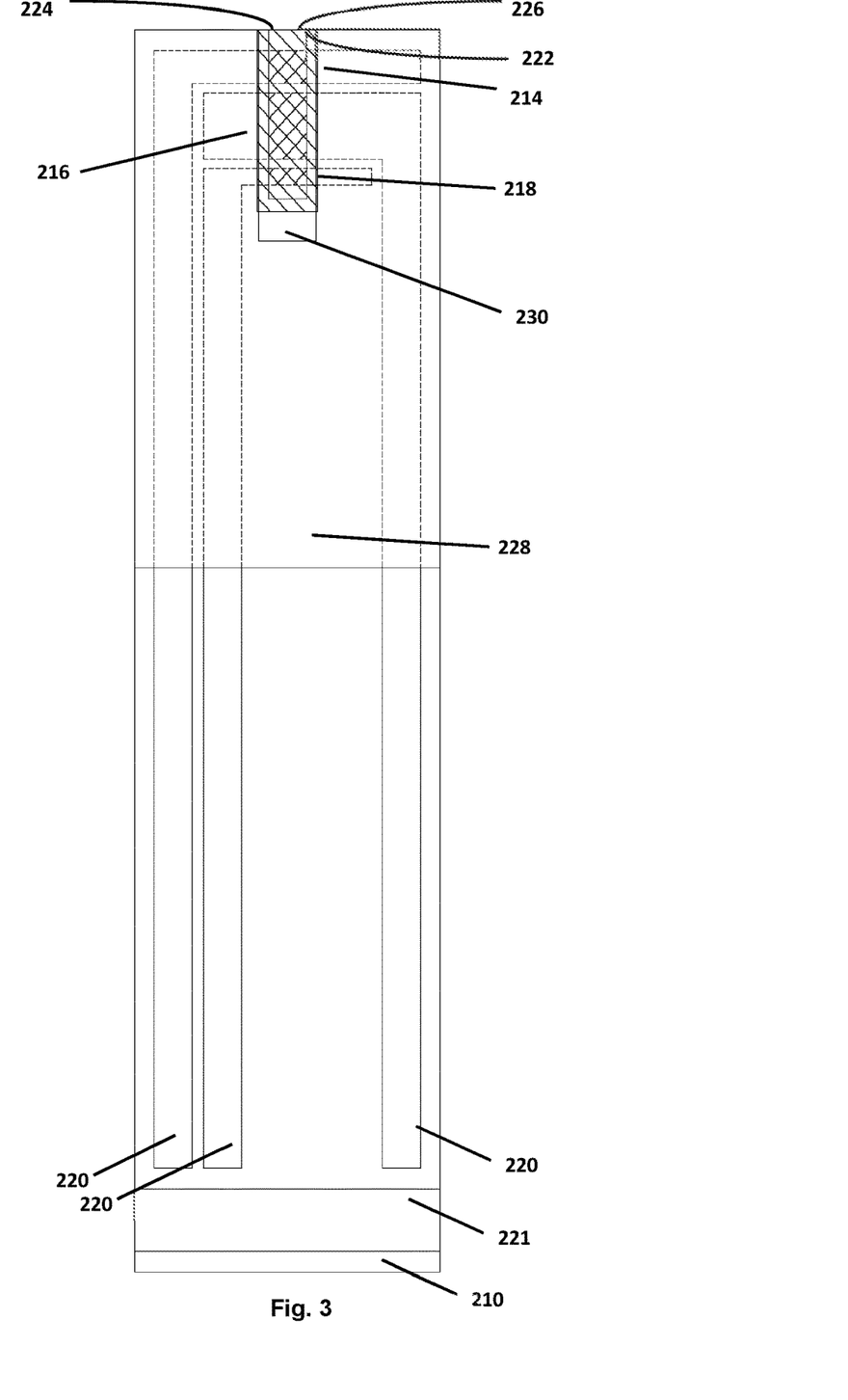
FIG. 3 shows a plan view of some layers of an electrochemical test device.

FIG. 3 depicts a plan view of some of the layers of the electrochemical test strip 200 of FIG. 2. In particular, FIG. 3 shows the substrate 210, the conductor layer 212, the insulator layer 222, the reagent layers 224 and 226, and the spacer layer 228. The cover layer 232 is not shown in FIG. 3 for clarity. The two reagent layers 224 and 226 are applied to the exposed areas of each of the working electrode 214, the counter/reference electrode 216 and the fill-sufficiency detect electrode 218.

Sensing chemistry for the electrodes according to some examples will now be described with reference to FIGS. 4 to 9. In particular, the sensing chemistry comprises a diaphorase and an electron transfer agent or mediator having a redox potential in the range −0.52 to 0.18 Volts using the standard redox potential range i.e. a standard hydrogen electrode (SHE) at Standard Temperature and Pressure (25° C. and 1 atm). The sensing chemistry further comprises an NAD(P)$^+$-dependent dehydrogenase and a cofactor.

Figure 4:
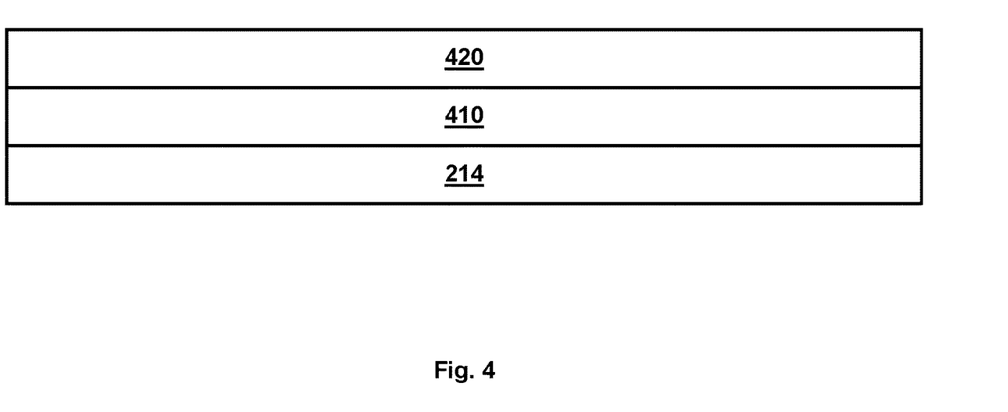
FIG. 4 shows reagent layers that may be applied to a working electrode.

The sensing chemistry may be applied in layers to the electrode(s) as illustrated in FIG. 4. FIG. 4 is a schematic showing reagent layers that may be applied to the working electrode 214 in order for an analyte to be detected (in the presence of a potential difference across electrodes). The first reagent print deposited onto the working electrode 214 is layer 410, also referred to as the "first layer" or "NAD(P)H detection layer". The first layer 410 is adjacent the electrode 214. The first layer 410 comprises a diaphorase and a mediator having a standard redox potential in the range of −0.52 to 0.18 Volts. The second reagent print applied to the electrochemical test device, which is deposited onto the first layer 410, is layer 420. Layer 420, is also referred to as the "second layer" or "analyte-sensitive layer". The second layer 420 is printed onto the NAD(P)H detection layer 410 positioned over the working electrode 214. The second layer 420 comprises NAD(P)$^+$ and a NAD(P)$^+$-dependent dehydrogenase suitable for detecting the analyte in question.

Figure 5:
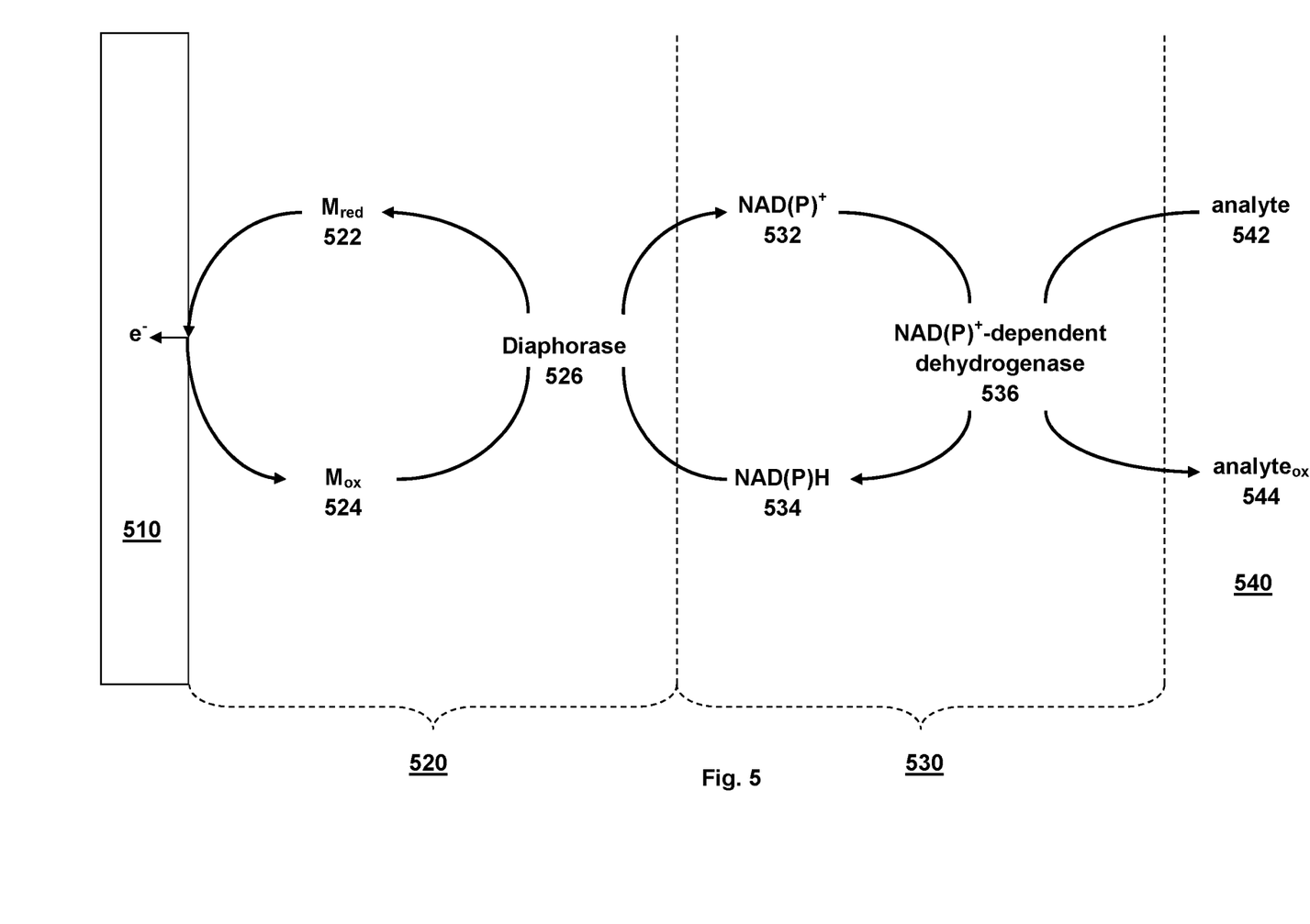
FIG. 5 illustrates bio-electrocatalysis at an electrode.

FIG. 5 is an illustration of bio-electrocatalysis at an electrode 510, which may correspond to working electrode 214 above, according to an example. In this example, electrode 510 is coated with NAD(P)H detection layer 520.

The NAD(P)H detection layer 520 is in contact with analyte-sensitive layer 530. Analyte-sensitive layer 530, when in the presence of a fluid sample 540 containing the analyte 542, is suitable for reacting with the analyte 542 in the fluid sample 540. The analyte-sensitive layer 530 comprises a NAD(P)$^+$-dependent dehydrogenase 536 and a cofactor NAD(P)$^+$ 532.

NAD(P)H detection layer 520 comprises a diaphorase 526 and an entrapped mediator (522, 524) which carry out the following reactions:

$$NADH + H^+ + Mediator \rightarrow NAD^+ + Reduced\ Mediator \quad (2)$$

$$NADPH + H^+ + Mediator \rightarrow NADP^+ + Reduced\ Mediator \quad (3)$$

Either NADH or NADPH may be used as reductants.

With reference to FIG. 5, when in the presence of a fluid sample 540, a cofactor NAD(P)$^+$ 532 and an applied potential difference, an NAD(P)$^+$-dependent dehydrogenase 536 of the analyte sensitive layer 530 interacts with the analyte 542 of the fluid sample 540. NAD(P)H 534 is produced as a result of the interaction, as is an oxidised form of the analyte 544. In the presence of a diaphorase 526 (which acts as a catalyst), an oxidised form of a mediator 524 in the NAD(P)H detection layer 520 reacts with the NAD(P)H 534 at the active site of the diaphorase 440 to produce a reduced mediator 522 and NAD(P)$^+$ 532. The reduced form of the mediator 522 then transfers electrons (e) to the electrode 510. In this way, the analyte-sensitive layer 530 and NAD(P)H detection layer 520 accelerate the transfer of electrons from the fluid sample 540 to the conducting electrode 510. A signal is thus generated to be detected by a strip meter.

The standard redox potential for the NADH/NAD$^+$ couple is approximately −0.315V. Known mediators include potassium ferricyanide which has a standard redox couple of approximately 0.436V, which represents an overpotential for the oxidation of NADH of approximately 0.6V. However, for a sensitive electrochemical test device, it is desirable to obtain an overpotential of less than approximately 0.5V.

In order to obtain an overpotential of less than 0.5V, electron transfer agents or mediators have been chosen carefully for the NAD(P)H detection layer 520. A minimum potential difference of around 0.2 Volts will be applied across the set of electrodes in order to ensure that the reactions occur at an appreciable rate. Additionally, an upper limit to the desired overpotential is defined by considerations of exogenous interference from compounds such as uric acid, which has a standard redox potential of around 0.59 Volts. Accordingly, a chosen mediator should preferably have a standard redox potential in the range of −0.52 to 0.18 V.

It is known that the standard redox potential of the mediator is important in determining the interference properties of the electrochemical test device, and so mediators with low redox potentials are preferred. In order to achieve the high sensitivity that is required to measure, for example, glycerol (typically 0.05 mM) or blood ketones such as the ketone body β-hydroxybutyrate (typically 0.1 mM) it is important that the mediator chosen to react with the diaphorase has a low standard redox potential so that any interference due to the oxidation of opportunist species is reduced.

The standard redox potential of ruthenium hexaammine trichloride is approximately 0.1 V, which corresponds to an overpotential of approximately 0.415V with respect to the NAD(P)$^+$/NAD(P)H couple. Such a low standard redox potential with respect to the NAD(P)$^+$/NAD(P)H couple is beneficial for the reasons stated above. In addition it is known that this molecule is stable over time, reacting little to, for example, moisture, sunlight, temperatures experienced during manufacture and conditions experienced in storage. Accordingly, the sensitivity of an electrochemical test device incorporating this mediator will not deteriorate rapidly over time. This feature is advantageous in designing a sensor which is to have a sub 1 mM limit of detection.

Other suitable mediators may be used. One such mediator is ruthenium pentaammine chloride, which has a standard redox potential of approximately −0.08V, which corresponds to an overpotential of approximately 0.235V with respect to the NAD(P)$^+$/NAD(P)H couple. NAD(P)H detection layer 520 may further contain buffer salts, fillers and stabilisers along with the enzyme diaphorase and a suitable mediator molecule.

The analyte-sensitive layer comprises NAD$^+$ and an NAD(P)$^+$-dependent dehydrogenase. As NAD$^+$ is included only in the analyte-sensitive reagent ink layer 530, not in a layer adjacent the electrode, current from direct oxidation of NAD$^+$ at the electrode is reduced thereby improving measurements of the analyte in the sample. Furthermore providing NAD$^+$ only in the analyte-sensitive layer 530 allows for an efficient use of the reagent, as the cofactor-dependent dehydrogenase is in close proximity to its cofactor which greatly simplifies the process of producing the electrochemical test device.

Figure 6:
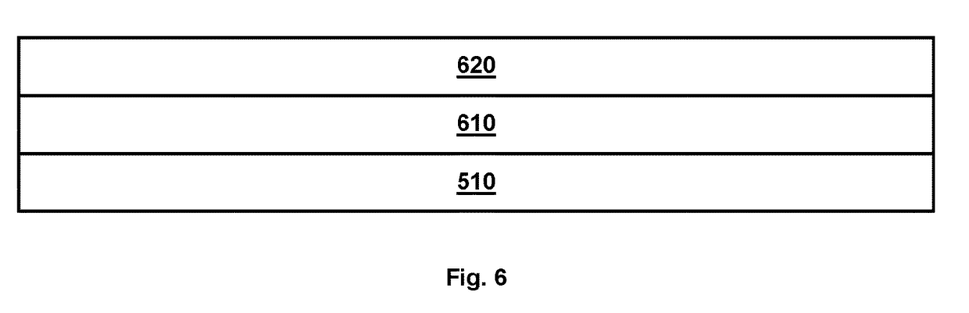
FIG. 6 shows reagent layers that may be applied to a working electrode.

FIG. 6 is a schematic showing the respective reagent layers applied to electrode 510 in an electrochemical test device for detecting the ketone body β-hydroxybutyrate, according to an example. In this example the analyte-sensitive ink layer 620 comprises NAD$^+$ dependent β-hydroxybutyrate dehydrogenase for reacting with β-hydroxybutyrate. The analyte-sensitive ink layer further comprises NAD$^+$. The analyte-sensitive layer may comprise one or more of a buffer, a gelling or thickening agent such as hydroxyetholcellulose (HEC) or other cellulosic polymers, a rheology/viscosity modifier such as silica, and a surfactant such as Tween 20. The analyte-sensitive layer reacts with β-hydroxybutyrate and produces NADH. The NADH detection layer 610 transfers electrons from the analyte-sensitive layer to the electrode 510.

The NADH detection layer 610 comprises a ruthenium-based compound, such as ruthenium hexaammine trichloride or ruthenium pentaammine chloride, and a diaphorase. The NADH detection layer may further comprise one or more of a buffer, HEC, silica, and Tween 20. The NADH detection layer 610 may further comprise flavin mononucleotide (FMN) for stabilising the diaphorase.

Figure 7:
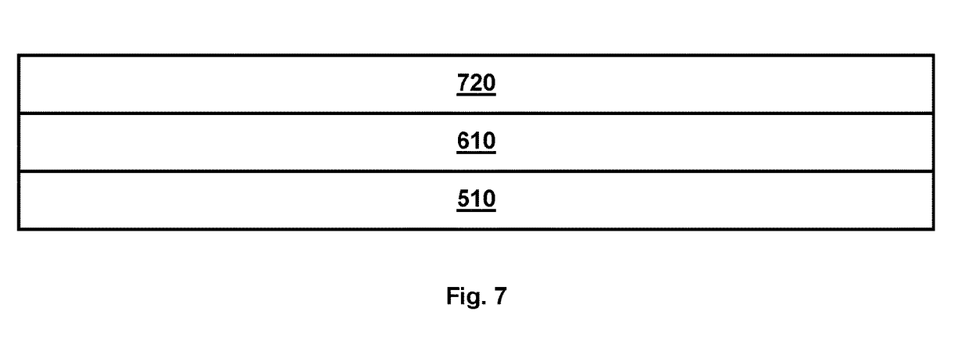
FIG. 7 shows reagent layers that may be applied to a working electrode.

FIG. 7 is a schematic showing the respective reagent layers applied to electrode 510 in an electrochemical test device for detecting glucose, according to an example. This example is similar to that discussed above in relation to FIG. 6 except for the properties of the analyte-sensitive layer. In this example the analyte-sensitive ink layer 720 comprises NAD$^+$ dependent glucose dehydrogenase (NAD-GDH) for reacting with glucose. The analyte-sensitive ink layer further comprises NAD$^+$. The analyte-sensitive layer may comprise one or more of a buffer, HEC, silica, and Tween 20. The analyte-sensitive layer reacts with glucose and produces NADH. The NADH detection layer 610 transfers electrons from the analyte-sensitive layer to the electrode 510.

Figure 8:
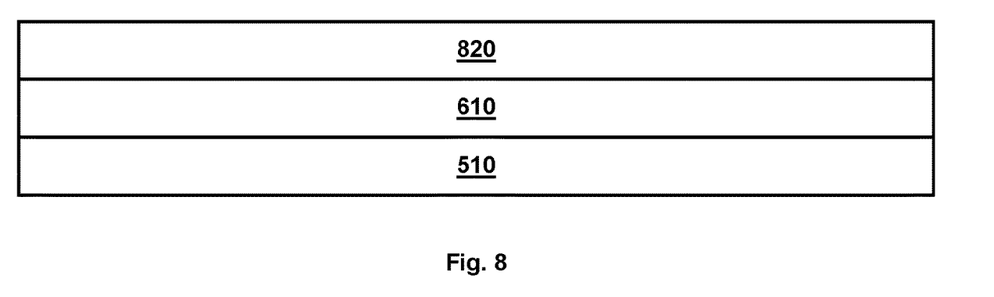
FIG. 8 shows reagent layers that may be applied to a working electrode.

FIG. 8 is a schematic showing the respective reagent layers applied to electrode 510 in an electrochemical test device for detecting glycerol, according to an example. This example is also similar to that discussed above in relation to FIG. 6 except for the properties of the analyte-sensitive layer. In this example the analyte-sensitive ink layer 820 comprises NAD$^+$ dependent glycerol dehydrogenase (GlyDH) for reacting with glycerol. The analyte-sensitive ink layer further comprises NAD$^+$. The analyte-sensitive layer may comprise one or more of a buffer, HEC, silica, and Tween 20. The analyte-sensitive layer reacts with glycerol and produces NADH. The NADH detection layer 610 transfers electrons from the analyte-sensitive layer to the electrode 510.

Figure 9:
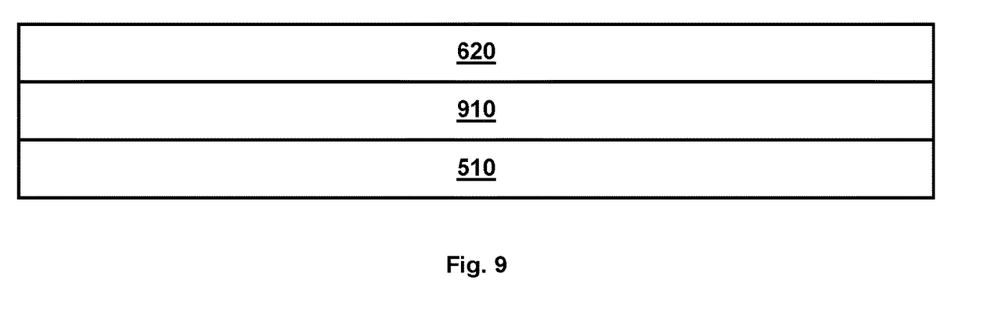
FIG. 9 shows reagent layers that may be applied to a working electrode.

In the examples discussed above in relation to FIGS. 6, 7 and 8, the NADH detection layer 610 has comprised a ruthenium based compound with a redox potential in the range of −0.52 to 0.18 V. Other compounds may be used as the electron transfer agent, as illustrated in FIG. 9. FIG. 9 is a schematic showing the respective reagent layers applied to electrode 510 in an electrochemical test device for detecting the ketone body β-hydroxybutyrate, according to an example. In this example the analyte-sensitive ink layer 620 comprises NAD$^+$ dependent β-hydroxybutyrate dehydrogenase for reacting with β-hydroxybutyrate and is the same as that discussed above in relation to FIG. 6. The NADH reaction layer 910 comprises a diaphorase and a mediator comprising osmium phendione.

Variations of the described embodiments are envisaged, for example, the features of all the disclosed embodiments may be combined in any way.

For example, an electrochemical test device may contain more layers than those disclosed in the preceding description. For example, an electrochemical test device may further comprise one or more bonding layers for bonding together one or more of the layers disclosed above. Additionally, some of the layers are not always necessary. For example, the insulator layer may be absent from the examples discussed above. The spacer layer may define the interaction area of the electrodes of the conductor layer beneath. The spacer layer may perform the dual role of receiving a fluid sample through a capillary channel and defining an interaction area for combining the fluid sample with the conductor layer. For example, the spacer layer can, with appropriate adhesive, define the active area/interaction area of the electrodes.

In the examples discussed above, a layer structure has been shown. The order in which each of the layers is formed may vary and any layer may, in some way, be configured so as to be in contact with any other layer.

The fluid sample may be a biological fluid. For example, the biological fluid may be blood, interstitial fluid, plasma, sweat, urine, lachrymal fluid, saliva or breath condensate. The analyte may be any analyte found in the fluid sample. For example, the analyte may be glucose, lactate, glycerol, cholesterol, or a ketone body such as β-hydroxybutyrate.

The electrochemical test device may be any suitable electrochemical test device. The electrochemical test device may be a test strip. In some examples the electrochemical test device may comprise a patch. Electrochemical test devices such as patches typically comprise a subcutaneous fluid extraction set and sensing chemistry for interaction with the analyte. The electrochemical test device may be a monitoring component which transmits an output signal to a separate device such as a meter, either wirelessly or through a wired connection. The electrochemical test device may comprise a continuous monitoring device or a semi-continuous monitoring device.

The electrochemical test device may be suitable for testing for multiple analytes. For example, the conductor layer may comprise a number of working electrodes, each working electrode featuring different sensing chemistry for detecting a different analyte. In particular, for each analyte there may be a dedicated working electrode of the conductor layer coated in a particular reagent suitable for reacting with the analyte.

In the example discussed above in relation to FIG. 2, the electrochemical test device had an end-fill configuration. In other embodiments, an electrochemical test device has a side-fill configuration i.e. the fluid sample is received at the side of the electrochemical test device.

The electrochemical test device may be suitable for measuring any fluid sample volume and may be of a suitable corresponding size for the volume. For example the electrochemical test device described in relation to FIG. 2 was arranged to receive approximately 0.5 µl of blood. The electrochemical test device may be scaled so as to receive other volumes including, for example, between 0.5 µl and 5 µl of a fluid, or between 0.5 µl and 1 µl of a fluid. The electrochemical test device may be scaled so as to receive less than 0.5 µl of a fluid, for example around 0.2 µl or around 0.3 µl.

Although in the discussion above in relation to FIG. 2 a fill-sufficiency detect electrode 218 was present, the fill-sufficiency detect electrode need not be present. Additionally, the fill-sufficiency detect electrode may or may not be coated in one or more reagent layers.

The analyte sensitive layer may be disposed upon the working electrode(s), the working electrode(s) and counter/reference electrode, or the working electrode(s), the counter/reference electrode and the fill-sufficiency detect electrode.

In the examples provided above, the conductor layer and the insulator layer are printed layers. The conductor layer and the insulator layer may be supplied using any suitable manufacturing technique. These include forms of printing, for example, screen printing, lithographic printing or tomographic printing. The conductor layer and the insulator layer need not be provided in the same way. Other suitable manufacturing techniques include etching, and/or sputtering, chemical vapour deposition or physical vapour deposition.

A conductor layer may be formed of any suitable conductor. For example, the conductor layer may be formed from a carbon based paste, such as a carbon/graphite paste, including graphene. The conductor layer may be formed of one or more metal based paste such as a gold, platinum or silver paste. Although the conductor layer 212 described above in relation to FIG. 2 comprises carbon-based ink, the conductors need not be formed from carbon based ink. For example, the electrodes may be formed of silver (Ag) or silver/silver chloride (Ag/AgCl). In some examples, the electrodes are formed of different conducting materials. The working electrode may, for example, be formed of carbon based ink whereas the counter/reference electrode may be formed of silver (Ag) or silver/silver chloride (Ag/AgCl).

The counter/reference electrode may be coated with a layer comprising an electron transfer agent. For example, an electrode formed from carbon based ink may be coated with a layer comprising mediator. The counter/reference electrode may not be coated in any sensing chemistry. For example, sensing chemistry may be absent from a counter/reference electrode formed of silver (Ag) or silver/silver chloride (Ag/AgCl).

The conductor layer may be of any suitable thickness. For example, the conductor layer may have a thickness greater than or equal to 0.005 mm and less than or equal to 0.030 mm.

The insulator layer may be formed of any suitable insulating material. For example, dielectric/insulation inks may be polymer loaded inks that are thermoplastic, thermoset or UV cured and that, when dried or cured, form a contiguous non-conductive layer. Examples include, Loctite EDAG PF 021 E&C and DuPont 5018.

In the examples discussed above, a polyester substrate layer was featured. Suitable substrate materials include polyester, polyimide, polystyrene, PVC, polycarbonate, glass and ceramic. When other layers are to be printed onto the substrate layer, the substrate layer has to be suitably printable for the chosen inks. The substrate must also be non-conductive. Typical thicknesses of the substrate layer range from 0.1 mm to 0.5 mm e.g. 0.35 mm. Glass and ceramic can be thicker as these are easier to handle with increased thickness. Thinner polymer substrates may be more difficult for the end user to use. Thicker substrates may offer some handling benefits.

The spacer layer may be formed of any suitable material. For example, the spacer layer may be made from a polyester core with a thin layer of PSA (Pressure Sensitive Adhesive) on either side. These adhesives can be the same or different depending on which layer is to be adhered to which side of the spacer layer.

Although in the examples above the thickness of the spacer layer was 0.1 mm, the thickness may vary. A typical range for the spacer layer thickness is 0.005-0.030 mm. Lower thicknesses may affect sensor performance and higher thicknesses would increase the volume of the sample introduction channel. A thickness of an adhesive on the spacer layer may contribute to the rigidity of the spacer layer.

Typically a spacer layer has a high volume resistivity. For example the volume resistivity may be greater than $1 \times 10^9$ Ωcm.

Other variations of the spacer layer are envisaged.

The sample introduction chamber may be provided along the longitudinal axis of the electrochemical device. The sample introduction chamber may be provided along the transverse axis of the electrochemical test device.

The vent may be of any suitable configuration for venting air from the sample introduction chamber. For example, the vent may comprise an air passageway in the cover. The vent may comprise an air passageway in the spacer layer. Optionally, air may be vented from the sample introduction chamber through one or more air passageways below the spacer layer, such as through the conductor layer or the insulator layer.

The sensing chemistry may include any suitable mediator having a standard redox potential in the desired range. In the examples described above, a ruthenium based electron transfer agent has been described. Other suitable mediators may be osmium based. For example, osmium phendione is a suitable mediator having a standard redox potential in the desired range. As another example, Os(4,4'-dimethyl-2,2'-bipyridine)$_2$ is a suitable mediator having a standard redox potential in the desired range.

The electron transfer agent may comprise a suitable quinone, for example a naphthoquinone derivative. The naphthoquinone derivative may be a 1,2 naphthoquinone derivative or a 1,4 naphthoquinone derivative. For example, the electron transfer agent may comprise 1,4 naphthoquinone-2-mercapto methyl carboxylic acid which has a standard redox potential of around −0.355V. The electron transfer agent may comprise 1,4 naphthoquinone-2-mercapto benzoic acid, which has a standard redox potential of around −0.345V. The electron transfer agent may comprise 1,2 naphthoquinone-4-sulphonate, which has a standard redox potential of around −0.214V. The electron transfer agent may comprise 1,4 naphthoquinone-2-mercapto methyl sulphonate. Also other suitable isomers of the above listed compounds are known which have similarly low standard redox potentials within the desired range.

In the examples above, the sensing chemistry is applied to the working electrode as two reagent layers. There may be more than two reagent layers. There may be only one reagent layer.

In the disclosure above, an NAD(P)$^+$-dependent dehydrogenase for reacting with an analyte was described. Examples of suitable NAD(P)$^+$-dependent dehydrogenases include glycerol dehydrogenase, glycerol-3-phosphate dehydrogenase, D-3-hydroxybutyrate dehydrogenase, glucose dehydrogenase (NAD Dependent), cholesterol dehydrogenase, lactate dehydrogenase, D-Lactate dehydrogenase, malate dehydrogenase, alcohol dehydrogenase and leucine dehydrogenase.

Further techniques may be used to enhance the sensitivity of any measurements made by the electrochemical test device. For example, the electrochemical test device may be configured to include a suitable delay before applying the voltage to the electrodes, during which the concentration of the measurand is allowed to accumulate at the working electrode surface.

Whilst the above examples have been described primarily in the context of an electrochemical test device for measuring a concentration of an analyte in a bodily fluid, it may equally be used in other fields, for example in health and fitness, food, drink, bio-security applications and environmental sample monitoring. The examples described herein may equally be used in the context of animal/veterinary medicine and fitness (including dogs and horses).

The above embodiments have been described by way of example only, and the described embodiments are to be considered in all respects only as illustrative and not restrictive. It will be appreciated that variations of the described embodiments may be made without departing from the scope of the invention.

The invention claimed is:

1. An electrochemical test device for determining a concentration of an analyte in a fluid sample, the electrochemical test device comprising a set of electrodes including a working electrode for the analyte and sensing chemistry for the working electrode, wherein the sensing chemistry is disposed on the working electrode in layers, wherein the sensing chemistry comprises a diaphorase, an electron transfer agent having a standard redox potential in the range of −0.52 to 0.18 V, an NAD(P)$^+$-dependent dehydrogenase and a cofactor for the NAD(P)$^+$-dependent dehydrogenase; and
wherein the layers include a layer which is not adjacent the working electrode, and the layer which is not adjacent the working electrode comprises the NAD(P)$^+$-dependent dehydrogenase, and wherein only the layer not adjacent the working electrode comprises the cofactor.

2. An electrochemical test device according to claim 1, wherein the test device is for determining a concentration of glycerol and the NAD(P)$^+$-dependent dehydrogenase is glycerol dehydrogenase.

3. An electrochemical test device according to claim 1, wherein the test device is for determining a concentration of β-hydroxybutyrate and the NAD(P)$^+$-dependent dehydrogenase is β-hydroxybutyrate dehydrogenase.

4. An electrochemical test device according to claim 1, wherein the test device is for determining a concentration of glucose and the NAD(P)$^+$-dependent dehydrogenase is NAD$^+$-glucose dehydrogenase.

5. An electrochemical test device according to claim 1, wherein a layer adjacent the working electrode comprises the diaphorase; and optionally;
wherein the layer adjacent the electrode also comprises the electron transfer agent.

6. An electrochemical test device according to claim 5, wherein the layers are two layers.

7. An electrochemical test device according to claim 1, wherein the electron transfer agent is ruthenium hexaammine trichloride.

8. An electrochemical test device according to claim 1, wherein the electron transfer agent is a quinone.

9. An electrochemical test device according to claim 8, wherein the electron transfer agent is a naphthoquinone derivative.

10. An electrochemical test device according to claim 9, wherein the naphthoquinone derivative is a 1,2 naphthoquinone derivative or a 1,4 naphthoquinone derivative.

11. An electrochemical test device according to claim 10, wherein the naphthoquinone derivative is 1,4 naphthoquinone-2-mercapto methyl carboxylic acid; or
wherein the naphthoquinone derivative is 1,4 naphthoquinone-2-mercapto benzoic acid; or
wherein the naphthoquinone derivative is 1,2 naphthoquinone-4-sulphonate; or
wherein the naphthoquinone derivative is 1,4 naphthoquinone-2-mercapto methyl sulphonate.

12. An electrochemical test device according to claim 1 wherein the electron transfer agent is a ruthenium- or osmium-based electron transfer agent.

13. An electrochemical test device according to claim 12, wherein the ruthenium- or osmium-based electron transfer agent is a complex of formula I, $$[M(A)_x(B)_y](X)_n \qquad \text{Formula I}$$

wherein
M is ruthenium or osmium;
A is an amine ligand;
each B is a ligand different to A;
x is an integer selected from 1 to 5;
y is an integer selected from 1 to 5;
x+y is 6 or 8;
n is an integer selected from 1 to 6;
X is any suitable counterion.

14. An electrochemical test device according to claim 13, wherein M is ruthenium.

15. An electrochemical test device according to claim 13, wherein B is halide, or optionally substituted heteroaryl; and optionally wherein B is chloride.

16. An electrochemical test device according to claim 13, wherein the ruthenium complex is [Ruthenium$^{III}$(NH$_3$)$_5$Cl]X.

17. An electrochemical test device according to claim 13, wherein the counterion X is selected from F$^-$, Cl$^-$, Br$^-$, I$^-$, PF$_6^-$; and optionally
wherein the ruthenium complex is [Ruthenium$^{III}$(NH$_3$)$_5$Cl]2Cl.

18. An electrochemical test device according to claim 12, wherein the oxidation state of the metal is selected to be 2+ or 3+.

19. An apparatus configured to determine the concentration of an analyte in a fluid sample applied to an electrochemical test device according to claim 1.

* * * * *